(12) United States Patent
Abe (10) Patent No.: US 7,498,135 B2
(45) Date of Patent: Mar. 3, 2009

(54) METHOD FOR PREPARING GENE EXPRESSION PROFILE

(75) Inventor: Masumi Abe, Chiba (JP)

(73) Assignee: National Institute of Radiological Sciences, Chiba (JP)

( * ) Notice: Subject to any disclaimer, the term of this patent is extended or adjusted under 35 U.S.C. 154(b) by 220 days.

(21) Appl. No.: 11/085,681

(22) Filed: Mar. 21, 2005

(65) Prior Publication Data

US 2005/0181424 A1    Aug. 18, 2005

Related U.S. Application Data

(63) Continuation of application No. PCT/JP2004/008439, filed on Jun. 16, 2004.

(30) Foreign Application Priority Data

Jun. 19, 2003    (JP)    ............... 2003-174895

(51) Int. Cl.
*C12Q 1/68*    (2006.01)
*C12P 19/34*    (2006.01)

(52) U.S. Cl. ............... 435/6; 435/91.1; 435/91.2

(58) Field of Classification Search .............. None
See application file for complete search history.

(56) References Cited

U.S. PATENT DOCUMENTS

2003/0022192 A1*    1/2003    Shi et al. ............... 435/6

FOREIGN PATENT DOCUMENTS

| CA | 2 431 170 | 6/2002 |
| EP | 1 348 762 A1 | 1/2003 |
| WO | WO 98/51789 | 11/1998 |
| WO | WO 02/48352 A1 | 6/2002 |

OTHER PUBLICATIONS

Fukumura et al. A sensitive transcriptome analysis method that can detect unknown transcripts. Nucleic Acids Res. (2003) 31:e94, pp. 1-7.*

Masumi Abe et al., "Jisedai Idenshi Hatsugen Profile Kaisekiho Michi Idenshi, Michi Tenshabutsu no Kenshutsu", Protein, Nucleic acid and enzyme (PNE) special extra issue, vol. 48 No. 11, Aug. 2003, pp. 1443-1449.

Masumi Abe et al., "Jisedai Idenshi Hatsugen Profile Kaisekiho Michi Idenshi, Michi Tenshabutsu no Kenshutsu", Protein, Nucleic acid and enzyme (PNE) special extra issue, vol. 4, No. 11, Aug. 2003, pp. 1443 to 1449.

International Search Report related to International Application PCT/JP2004/008439.

Supplemental European Search Report related to EP 04 74 5980.

* cited by examiner

*Primary Examiner*—Kenneth R. Horlick
*Assistant Examiner*—David C Thomas
(74) *Attorney, Agent, or Firm*—Husch Blackwell Sanders llp Welsh & Katz (57) ABSTRACT

The present invention provides a method for preparing a gene expression profile with a high precision, by carrying out the annealing of primers to templates in the temperature range of TmMAX+6° C. to TmMAX+14° C. of the primer in a PCR step of a HiCEP method.

3 Claims, 3 Drawing Sheets

FIG. 2
PRIMER SET CG-TA (TmMAX=64°C)
THE ANNEALING TEMPERATURE OF 70°C

METHOD FOR PREPARING GENE EXPRESSION PROFILE

This is a continuation application of PCT/JP4/008439 with an International Filing Date of Jun. 16, 2004.

TECHNICAL FIELD

The present invention relates to a method for preparing a gene expression profile.

BACKGROUND ART

In the year 2002, the human genome sequence has been decoded almost completely. From the obtained data of bases, the developments of tailor-made therapies and so on have been expected. For this purpose, it is very important to identify genes and determine the degree of their expression in vivo, or to elucidate the network of gene expression. In addition, for elucidating the gene-expression network, there is a need for making a gene expression profile, which identifies genes being expressed and determines the degree of their expression in vivo at a specified time.

At present, methods for preparing a gene expression profile include a differential display method, a serial analysis of gene expression (SAGE), a method using a micro-array or a DNA chip, a method of high-coverage expression profiling (Hi-CEP) disclosed in the International Publication WO 02/48352 A1, etc.

Among these methods for preparing a gene expression profile, the HICEP method is an excellent one in that the gene expression profile can be easily prepared for covering a wide variety of genes including unknown genes.

In a PCR reaction used as one of the steps in the HiCEP method, the temperature used for annealing a primer to a template is conventionally around the melting temperature (Tm) of the primer, for example, 55° C. when each primer used was composed of a 20 mer with a 50% GC content ("Protocol 15: Quantitative PCR 8.86" in Sambrook and Russell, "Molecular Cloning", 3rd Ed., Cold Spring Harbor Laboratory Press (U.S.A.), 2001).

The expression level of a gene varies depending on the kinds of genes and the expression timing thereof. Therefore, for elucidating the gene expression network, a method for preparing a gene expression profile, as a prerequisite thereof, is desired to have high detection sensitivity to expressed genes.

Accordingly, for a HiCEP method capable of preparing a gene expression profile covering a wide variety of genes in a simple manner, the present inventor has intensively studied for a further improvement in the sensitivity of detecting expressed genes.

DISCLOSURE OF THE INVENTION

As a result, in the PCR reaction step of the HiCEP method, the present inventor has found that a dramatic improvement in the detection sensitivity of expressed genes can be attained by setting the annealing temperature of a primer to a template used in the PCR reaction in a particular range. The present invention has been accomplished based on these findings.

That is, the present invention is a method for preparing a gene expression profile, which is characterized by comprising:

(a) synthesizing a single-stranded cDNA by using a poly (A) RNA as a template, wherein the single-stranded cDNA bearing a tag substance at the 5'-end side relative to the single-stranded cDNA is synthesized;

(b) synthesizing a double-stranded cDNA by using the single-stranded cDNA synthesized in the step (a) as a template, wherein the double-stranded cDNA bearing a tag substance at the 3'-end side relative to the double-stranded cDNA is obtained;

(c) cleaving the double-stranded cDNA obtained in the step (b) with a first restriction enzyme X;

(d) recovering a fragment bearing the tag substance from fragments obtained in the step (c) by using a substance having a high affinity for the tag substance;

(e) ligating an adaptor X containing a sequence complementary to the sequence of the cleavage site and a sequence complementary to the sequence of a primer X to the cleavage site of the fragment generated by the first restriction enzyme X as recovered in the step (d), to obtain a fragment ligated with the adaptor X at the 5'-end side relative to the double-stranded cDNA;

(f) cleaving the fragment recovered in the step (e) with a second restriction enzyme Y that does not cleave the adaptor X;

(g) removing a fragment bearing the tag substance from the fragments obtained in the step (f) by using a substance having a high affinity for the tag substance, to recover a fragment containing the cleavage site generated by the second restriction enzyme Y at the 3'-end side relative to the double-stranded cDNA;

(h) ligating an adaptor Y containing a sequence complementary to the sequence of the cleavage site and a sequence complementary to the sequence of a primer Y to the cleavage site of the fragment generated by the second restriction enzyme Y as recovered in the step (g), to obtain a fragment of a double-stranded sequence ligated with the adaptor Y at the 3'-end side relative to the double-stranded cDNA;

(i) performing a PCR reaction with the fragment of the double-stranded sequence obtained in the step (h) as a template by using a primer set composed of a primer X containing a sequence complementary to the sequence of the adaptor X, which has the sequence of 2 bases $N_1N_2$ ($N_1$ and $N_2$ may be identical or different bases that are selected from the group consisting of adenine, thymine, guanine and cytosine) at the 3' end relative to the primer X, and a primer Y containing a sequence complementary to the sequence of the adaptor Y, which has the sequence of 2 bases $N_3N_4$ ($N_3$ and $N_4$ may be identical or different bases that are selected from the group consisting of adenine, thymine, guanine and cytosine) at the 3' end relative to the primer Y; and (j) subjecting the obtained PCR product to electrophoresis and detecting the migration distance and peaks to prepare a gene expression profile, wherein, in the step (i), the annealing of the primer X and the primer Y to the adaptor X and the adaptor Y respectively is carried out in the temperature range of TmMAX+6° C. to TmMAX+14° C. of the primers.

BEST MODE FOR CARRYING OUT THE INVENTION

A method for preparing the gene expression profile of the present invention will be described with reference to FIG. 1 as one embodiment. The alphabets of the above-mentioned steps from (a) to (j) correspond to those of steps (a) to (j) in FIG. 1, respectively.

Figure 1:
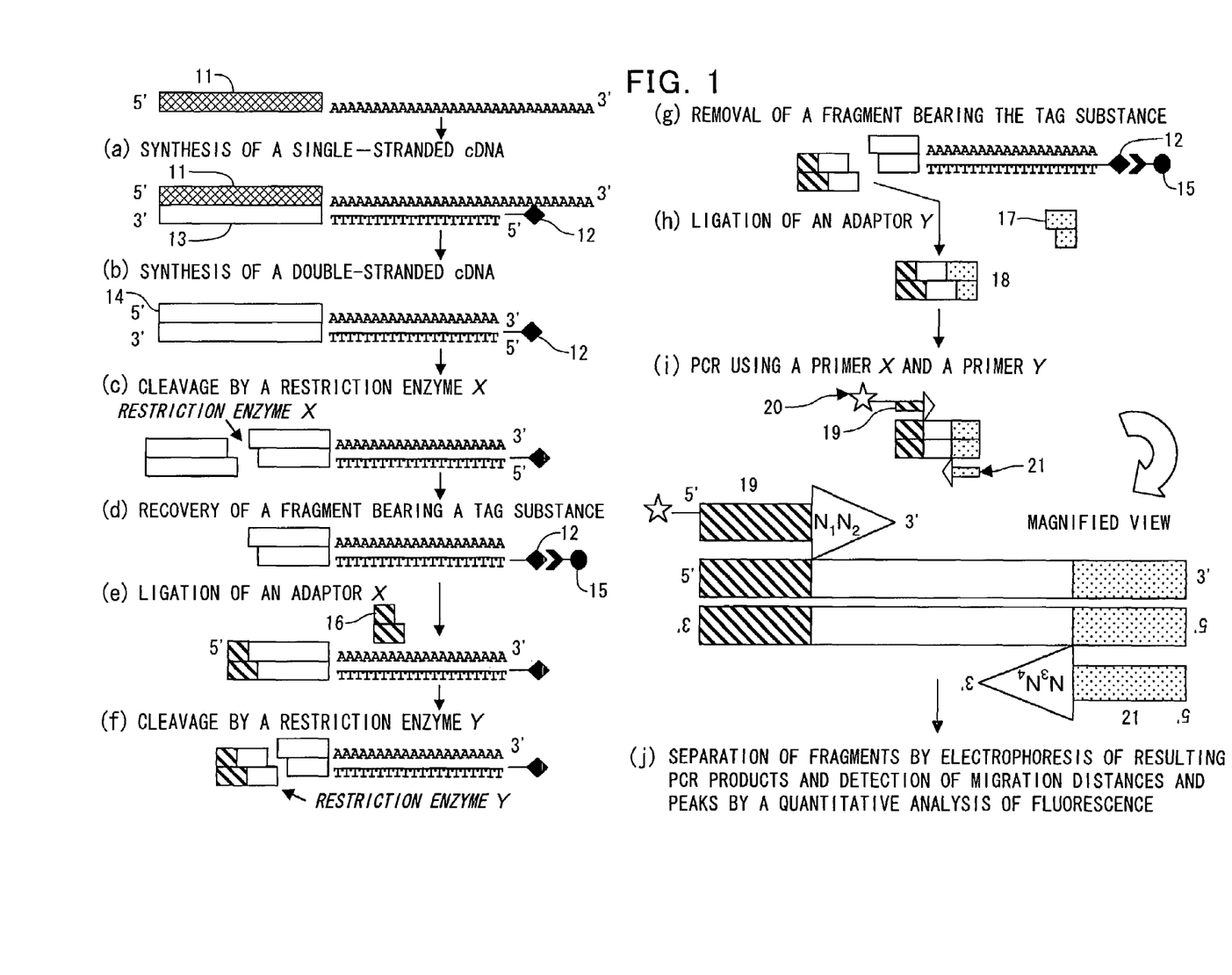
FIG. 1 is a schematic diagram showing a method for preparing a gene expression profile, which is one embodiment of the present invention.

Each of the alphabets of sequences shown in FIG. 1 represents a base constituting a base sequence. A represents adenine (hereinafter, abbreviated to A); G represents guanine (hereinafter, abbreviated to G); C represents cytosine (hereinafter, abbreviated to C); and T represents thymine (hereinafter, abbreviated to T). $N_1$, $N_2$, $N_3$, and $N_4$ each may be identical or different, which are bases selected from the group consisting of A, C, G, and T.

In the description of the present invention, the 5'-end side of a sense strand (a strand having a sequence homologous to a poly(A) RNA as a template) of a double-stranded cDNA is given as the 5' end of the double-stranded cDNA and the 3' end of the sense sequence is given as the 3' end of the double stranded cDNA unless otherwise specified herein.

Step (a)

In this step, a poly(A) RNA is used as a template to synthesize a single-stranded cDNA.

First, a poly(A) RNA 11 is extracted from a cell targeted for preparing a gene expression profile.

An oligo dT primer complementary to a poly(A) tail at the 3'-end side of the extracted poly(A) RNA 11, which is labeled with a tag substance 12, is used as a primer to synthesize a single-stranded cDNA 13 (shown together with the poly(A) RNA 11 in FIG. 1) with the poly(A) RNA 11 as a template. The tag substance 12 is added at the 5'-end side relative to the single-stranded cDNA 13.

Step (b)

The single-stranded cDNA 13 synthesized in the step (a) is used as a template to synthesize a double-stranded cDNA 14. The tag substance 12 is added at the 3'-end side relative to the double-stranded cDNA 14.

Step (c)

The double-stranded cDNA 14 obtained in the step (b) is cleaved with a first restriction enzyme X.

Step (d)

Using a substance 15 having a high affinity for the tag substance 12, the tag substance 12 is captured to recover a fragment bearing the tag substance 12 from the fragments obtained in the step (c).

Step (e)

To a cleavage site of the fragment generated by the first restriction enzyme X as recovered in the step (d), an adaptor X 16 containing a sequence complementary to the sequence of the cleavage site and a sequence complementary to the sequence of a primer X is ligated to obtain a fragment ligated with the adaptor X 16 at the 5'-end side relative to the double-stranded cDNA 14.

Step (f)

The fragment recovered in the step (e) is cleaved with a second restriction enzyme Y.

Step (g)

The substance 15 having a high affinity for the tag substance 12 is used to remove a fragment bearing the tag substance 12 from the fragments obtained in the step (f), thereby recovering a fragment containing a cleavage site by the second restriction enzyme Y at the 3'-end side relative to the double-stranded cDNA 14.

Step (h)

To the cleavage site of the fragment generated by the second restriction enzyme Y as recovered in the step (g), an adaptor Y 17 containing a sequence complementary to the sequence of the cleavage site and a sequence complementary to a primer Y is ligated to obtain a fragment 18 of a double-stranded sequence ligated with the adaptor Y 17 at the 3'-end side relative to the double stranded cDNA 14. The obtained fragment 18 of the double-stranded sequence contains the adaptor X 16 at the 5'-end side and the adaptor Y 17 at the 3'-end side relative to the double-stranded cDNA 14.

Step (i)

Using a primer set composed of a primer X 19 containing a sequence complementary to the sequence of the adaptor X 16, which has the sequence of 2 bases $N_1N_2$ (wherein $N_1$ and $N_2$ may be identical or different bases that are selected from the group consisting of A, T, G, and C) at the 3' end (i.e., at the amplification side) relative to the primer X 19 and is bonded with a fluorescent substance 20 at the 5' end relative to the primer X 19, and a primer Y 21 containing a sequence complementary to the sequence of the adaptor Y 17, which has the sequence of 2 bases $N_3N_4$ (wherein $N_3$ and $N_4$ may be identical or different bases that are selected from the group consisting of A, T, G, and C) at the 3' end (i.e., at the amplification side) relative to the primer Y 21, a PCR reaction is carried out with the fragment 18 of the double-stranded sequence obtained in the step (h) as a template.

Here, the temperature for annealing the primer set to the template is in the range of Tm MAX+6° C. to Tm MAX+14° C. of the primers.

Step (j)

The obtained PCR product is subjected to electrophoresis to detect the migration distance and peaks, and a gene expression profile is prepared.

In the present specification, a "gene expression profile" refers to any of those showing information such as an expression pattern of a gene in a specified cell under certain conditions, the presence or absence of an expression of a known or unknown gene, the expression level of all genes being expressed, etc. In addition, the gene expression profile may be utilized as a means for analyzing the expression of genes.

A "poly(A) RNA" refers to an mRNA having a sequence called generally polyA at the 3' end. Moreover, a cDNA can be synthesized from the poly(A) RNA with an "oligo dT primer" having a sequence complementary to the poly(A) RNA. Generally, the "oligo dT primer" used here is also referred to as an oligo(dT) primer. The synthesis of a single-stranded cDNA from the poly(A) RNA using the oligo dT primer (step (a)) may be achieved under any of generally employed conditions. The synthesis of a double-stranded cDNA from the single-stranded cDNA (step (b)) may also be achieved under any of generally employed conditions.

A "tag substance" or a "substance having a high affinity for the tag substance" refers to either of substances constituting a binding pair capable of specifically binding to each other with a high affinity. In the method shown in Example 1 according to one embodiment of the present invention, biotin as the tag substance and streptavidin as the substance having a high affinity for the tag substance are used, but not limited to them. Any of binding pairs capable of specifically binding to each other with a high affinity may be used. Examples of the combination of the tag substance with the substance having a high affinity for the tag substance available in the present invention include, but not limited to, biotin and streptavidin, biotin and avidin, FITC and a FITC antibody, DIG and anti-DIG, Protein A and mouse IgG, latex particles, etc. The addition of the tag substance to a DNA sequence may be achieved under any of generally employed conditions. Furthermore, the recovery of a DNA fragment based on an affinity between the "tag substance" and the "substance having a high affinity for the tag substance" (steps (d) and (g)) may be achieved under any of generally employed conditions.

A "restriction enzyme" is an enzyme generally called as a restriction endonuclease, which hydrolyzes and cleaves a double-stranded DNA in a certain sequence. In the present invention, for obtaining suitable fragments, two restriction enzymes X and Y are utilized in combination. It is preferable that a restriction enzyme useful in the present invention is an enzyme capable of cleaving a double-stranded cDNA synthesized from an expressed gene, that is, an mRNA, into fragments each having a recognizable length. Also preferable is an enzyme capable of cleaving as many of the obtained double strands as possible, preferably almost all of the double strands. Examples of such an enzyme are shown in Table 1 described below.

| Restriction Enzyme Name | Recognition Site of Restriction Enzyme | Restriction Enzyme Name | Recognition Site of Restriction Enzyme |
|---|---|---|---|
| AccII | CG/CG | HpaII | C/CGG |
| AfaI | GT/AC | Hsp92II | CATG/ |
| AluI | AG/CT | HspAI | G/CGC |
| AspLEI | GCG/C | Kzo9I | /GATC |
| BfaI | C/TAG | MaeI | C/TAG |
| BscFI | /GATC | MboI | /GATC |
| Bsh1236I | CG/CG | MseI | T/TAA |
| BshI | GG/CC | MspI | C/CGG |
| BsiSI | C/CGG | MvnI | CG/CG |
| Bsp143I | /GATC | NdeII | /GATC |
| BstUI | CG/CG | NlaIII | CATG/ |
| BsuRI | GG/CC | PalI | GG/CC |
| CfoI | GCG/C | RsaI | GT/AC |
| Csp6I | G/TAC | Sau3AI | /GATC |
| DpnII | /GATC | Sse9I | /AATT |
| FnuDII | CG/CG | TaqI | T/CGA |
| HaeIII | GG/CC | ThaI | CG/CG |
| HapII | C/CGG | Tru1I | T/TAA |
| HhaI | GCG/C | Tru9I | T/TAA |
| Hin2I | C/CGG | Tsp509I | /AATT |
| Hin6I | G/CGC | TspEI | /AATT |
| HinP1I | G/CGC | TthHB8I | T/CGA |

Any two of enzymes may be selected from enzymes of Table 1 and used in combination. Also, although enzymes shown in Table 1 are enzymes recognizing 4 bases, other enzymes recognizing 4 bases or enzymes recognizing 6 bases may be used. In the present invention, it is preferable to use the enzyme recognizing 4 bases and it is particularly preferable to use a combination of MspI and MseI. In the method shown in Example 1 according to one embodiment of the present invention, MspI is used as the restriction enzyme X and MseI is used as the restriction enzyme Y, but the enzymes are not limited to them. The cleavage of a double-stranded DNA by the restriction enzyme (steps (c) and (f)) may be achieved under any of generally employed conditions.

An "adaptor" is used for binding of a primer used in a PCR reaction in the step (i). The adaptor is designed in accordance with restriction enzymes and primers used. That is, an adaptor X to be ligated to a recognized cleavage site of a restriction enzyme X contains a sequence complementary to the recognized cleavage site of the restriction enzyme X and further has a sequence complementary to the sequence of a primer X. Preferably, the adaptor X can be designed to have around 30 bases. This enables performing a stable PCR. An adaptor Y to be ligated to a recognized cleavage site of a restriction enzyme Y contains a sequence complementary to the recognized cleavage site of the restriction enzyme Y and further has an arbitrary sequence complementary to a primer Y. Preferably, the adaptor Y can be designed to have around 30 bases. This enables performing a stable PCR.

In the method of Example 1 according to one embodiment of the present invention, as the adaptor X, those containing a sequence complementary to a cleavage site by the restriction enzyme MspI (SEQ ID NOs: 1 and 2), and, as the adaptor Y, those containing a sequence complementary to a cleavage site by the restriction enzyme MseI (SEQ ID NOs: 3 and 4) are used, but the adaptors are not limited to them. The binding of the adaptor to a double-stranded DNA (steps (e) and (h)) may be achieved under any of generally employed conditions.

In each of X- and Y-primer sequences which constitute a set of primers used in a PCR reaction in the step (i), the sequence of the part of each primer other than the two-base sequence part ($N_1N_2$ for the primer X and $N_3N_4$ for the primer Y) at the 3' end of each primer is desired not to coincide with the sequence of a subject RNA. However, it is difficult to satisfy this condition because the whole RNA sequence has not been elucidated in any organisms until now. Therefore, for example, if a human subject is used for study, it is preferable to select a sequence which is absent or occurring with an extremely low frequency in the human genome sequence.

For satisfying the above-described condition, it is preferable that the primer X and the primer Y each have a length of 16 bases or more. For example, if a primer is designed with a length of 16 bases under the circumstance that the human genome sequence has a length of approximately 3 billion bases, 4 to the 16th power of (approximately 4 billion different) primers are made possible from 4 bases (A, C, G, and T) constituting the primer, and therefore an arbitrary primer having 16 bases selected from these primers will occur in the human genome sequence with the frequency of 1 or less. Thus, by comparing the sequence of a primer having a length of 16 bases or more designed in consideration of general conditions required for a primer, which will be described below, with the sequences registered in a publicly available base sequence database, a primer having a sequence not coinciding with the sequences present in the human genome or a sequence occurring with an extremely low frequency can be selected.

Besides, a primer used in the step (i) has to satisfy conditions generally required for a PCR primer (e.g., conditions described in Hiroki Nakayama, "Bio Experiment Illustrated (3), New Edition, PCR capable of really amplifying (Hontouni Fueru PCR in Japanese)," 2nd Ed., Fourth impression, Shunjunsha, 2002):

1. Formation of a primer-dimer is not expected to occur between primers X, between primers Y, and between a primer X and a primer Y;
2. Formation of a higher-order intramolecular structure is not expected to occur in a primer X and in a primer Y; and
3. Complementarity of 5'-end sequences is not expected to occur between primers X, between primers Y, and between a primer X and a primer Y.

For a Tm value of the primer, because the Tm value defines an annealing temperature (from TmMAX+6° C. to TmMAX+14° C. of the primer), the annealing temperature increases as the Tm value of the primer increases. Therefore, the Tm value of the primer is preferably equal to or lower than the maximum temperature minus 6° C. at which a heat resistant polymerase being used sufficiently functions throughout the whole reaction time in a PCR reaction, so that the annealing temperature does not exceed the temperature at which the heat resistant polymerase can sufficiently function throughout the whole reaction time in the PCR reaction. Accordingly, it is preferable that the Tm values of primers X and Y used in the step (i) each are in the range of 59° C. to 69° C., especially in the range of 60° C. to 64° C. When the Tm value of each of the primer X and the primer Y is in the range of 60 to 64° C., a PCR reaction can be carried out with an annealing temperature (from TmMAX+6° C. to TmMAX+14° C.) described below to obtain substantially high detection sensitivity of expressed genes.

The sequence of 2 bases at the 3'-end side of each of primers X and Y ($N_1N_2$ for the primer X and $N_3N_4$ for the primer Y) may be identical or different, which are bases selected from the group consisting of adenine, thymine, guanine and cytosine.

The primer X and the primer Y can be synthesized using a general method for synthesizing primers, for example, the chemical synthesis method of oligonucleotides by a phosphoramidite approach (Letsinger et. al., Nucleic Acids Research, 20, 1879-1882, 1992) and a method described in Unexamined Japanese Patent Publication No. 11-08018.

Moreover, for facilitating detection after a PCR reaction, it is preferable to previously bind a fluorescent substance to the end of either of the primers. Preferably, the fluorescent substance is bonded to the 5' end of the primer X. A fluorescent substance that may be used in the present invention includes 6-carboxyfluorescein (FAM), 4,7,2',4',5',7'-hexachloro-6-carboxyfluorescein (HEX), NED (Applied Biosystems, Japan), 6-carboxy-X-rohdamine (Rox), etc.

A "primer set" refers to one set of primers composed of a primer X and a primer Y used for carrying out a PCR reaction with a fragment of a double-stranded sequence obtained in the step (h) as a template. Here, in the case of using, as the primers X and Y constituting the primer set, primers each having a fixed structure of sequences other than the sequence of 2 bases ($N_1N_2$ for the primer X and $N_3N_4$ for the primer Y) at the 3'-end side of each primer sequence (e.g., an Mspl primer shown in SEQ ID NO.: 5 as a primer X used in Example 1, and a Msel primer shown in SEQ ID NO.: 6 as a primer Y used in Example 1), 16 different primers X and 16 different primers Y can be obtained depending on the kinds of bases constituting the 2-base sequence. Combinations of these primers X and Y result in 256 different primer sets. It is preferable to use such 256 different primer sets because gene expression profiles covering the expression of almost all of genes can be prepared in a simple manner.

The step (j), a means "subjecting the obtained PCR product to electrophoresis and detecting the migration distance and peaks to prepare a gene expression profile" may be any of those capable of measuring the molecular weight (the length of a base sequence) and the quantity of an amplified PCR product. Among them, electrophoresis is preferable in terms of high resolution, and gel electrophoresis is particularly preferable. When gel electrophoresis is used, a gel electrophoresis device can be combined with analysis software to obtain the results of gel electrophoresis as a peak pattern that is an indicator of the migration distance and the quantity of the separated PCR amplification product. In this peak pattern, the migration distance of an amplified PCR product reflects a certain gene and the quantity of the amplified PCR product reflects the expression level of the gene. Accordingly, the peak pattern is given as a gene expression profile itself.

As the gel electrophoresis device, for example, ABI PRISM 3100 (Applied Biosystems, Japan), ABI PRISM 3700 (Applied Biosystems, Japan), and MegaBASE 1000 (Amersham Pharmacia), which are called as a sequencer, can be used. As the analysis software, for example, GeneScan™ (Applied Biosystems, Japan) can be used.

Furthermore, it is noted that each of the above-described steps can be also carried out according to a method described in the International Publication WO 02/48352 A1.

In addition, the magnitude of a peak which appears on the gene expression profile prepared according to the present invention reflects the expression level of a gene expressed in a subject cell. Thus, the frequency of the gene expression can be analyzed by observing changes in the magnitude of the peak. It is possible to carry out, for example, comparison between a normal cell and an abnormal cell, comparison between a normal cell and a canceer cell, comparison between different cells, comparison between cells treated under different conditions, etc.

Hereinafter, an annealing temperature in the step (i) that characterizes the present invention will be described in detail.

In a PCR reaction of the step (i), the annealing of a primer set to templates, that is, the annealing of a primer X and a primer Y constituting the primer set to each of the corresponding strands of a fragment of a double-stranded sequence obtained in the step (h) is carried out in the temperature range of TmMAX+6° C. to TmMAX+14° C. of the primer, preferably in the range of TmMAX+6° C. to TmMAX+10° C. of the primer, and most preferably in the range of TmMAX+6° C. to TmMAX+9° C. of the primer.

Here, the "TmMAX" of the primer refers to the larger one of the Tm values of a primer X and a primer Y constituting a primer set. Moreover, the "Tm" of the primer refers to a temperature at which a double strand formed by a primer and an adaptor is unraveled. Tm can be experimentally determined according to a method described in, for example, Shoji Mizushima, Tairo Oshima, et. al., "Basic Experiment of Life Science (Raifu Saiensu no Kiso Jikken in Japanese)", Maruzen. Alternatively, if the number of bases constituting a primer is less than 20, Tm can be calculated most easily according to, for example, the following formula described in Chapter 10.3 in Sambrook and Russel, "Molecular Cloning" 3rd Ed., Cold Spring Harbor Laboratory Press (U.S.A.), 2001:

$$Tm(° C.) = 2 \times (A+T) + 4 \times (G+C) \quad \text{(Formula 1)},$$

wherein (A+T) is the sum of the numbers of adenine (A) and thymine (T) residues constituting a primer; and (G+C) is the sum of the numbers of cytosine (C) and guanine (G) residues.

As described above, although Tm can be experimentally and computationally determined and there are various methods for determination, any of the methods can be utilized as long as the same method is used to determine Tm of a primer X and Tm of a primer Y.

If several different primer sets are simultaneously used, the largest one of the Tm values of a primer X and a primer Y constituting each primer set used is given as TmMAX. When the annealing of the primer set of the present invention is carried out in the temperature range of TmMAX+6° C. to TmMAX+14° C. of the primer, misannealing can be avoided, resulting in an improvement of the detection sensitivity of an expressed gene.

It is noted that if only the correct annealing of primers to templates is desired, this purpose is considered to be attained by using an annealing temperature of TmMAX+6° C. or more of the primer.

However, the enzyme activity of a heat resistant polymerase used in a PCR reaction is affected by temperature and the heat resistant polymerase is reduced in function under high temperatures at which enzymes are denatured (e.g., 90° C. or more for a Taq polymerase), leading to the reduction in the efficiency of the PCR reaction. Thus, it is necessary to set the annealing temperature at or below the temperature at which a heat resistant polymerase can sufficiently function throughout the whole reaction time in the PCR reaction (e.g., 75° C. for the Taq polymerase).

In light of the foregoing, in the present invention, an annealing temperature in the step (i) is set in the temperature range of TmMAX+6° C. to TmMAX+14° C. of the primer, and preferably in the range of TmMAX+6° C. to TmMAX+9° C. of the primer, at which the correct annealing of primers to templates can be attained while a heat resistant polymerase can sufficiently function and a substantial improvement of detection sensitivity of an expressed gene can be accomplished. Incidentally, as the conditions of a PCR reaction except for the above-mentioned annealing temperature, conditions employed generally for a PCR reaction can be used.

In Example 1 according to one embodiment of the present invention, as a primer X, a primer having a sequence complementary to an adaptor X containing a sequence complementary to a cleavage site by a restriction enzyme MspI (SEQ ID NO.: 5), and as a primer Y, a primer having a sequence complementary to an adaptor Y containing a sequence complementary to a cleavage site by a restriction enzyme MseI (SEQ ID NO.: 6) are used. In this case, the Tm values of the primer X and the primer Y calculated according to the above formula (1) are in the range of 60° to 64° C. (i.e., TmMAX=64° C.), and thus the annealing temperature is in the range of 70° C. (TmMAX+6° C.) to 78° C. (TmMAX+14° C.), but not limited to them.

In the preferred embodiment of the present invention, in the step (i), by using an adaptor having sequences shown in SEQ ID Nos: 1 and 2 as an adaptor X, and an adaptor having sequences shown in SEQ ID NOs:3 and 4 as a primer Y, and by using 256 different primer sets composed of, a primer having a sequence shown in SEQ ID NO: 5 as a primer X and a primer having a sequence shown in SEQ ID No: 6 as a primer Y, a PCR reaction is carried out at the temperature for annealing primers in the range of 70° C. (TmMAX+6° C.) to 73° C. (TmMAX+9° C.).

EXAMPLES

Next, the effect of the present invention will be specifically explained with reference to examples. However, the present invention is not intended to be limited to them.

As an indicator of the detection sensitivity of an expressed gene, the presence of a false peak in a gene expression profile is adopted.

A peak in the gene expression profile is a peak that corresponds to the quantity of a PCR product (a gene transcript) obtained by amplification in a PCR reaction of the step (i) of the present invention, and can be detected based on, for example, a fluorescent dye bonded to the 5'-end side of a primer X.

A false peak refers to a peak generated by misannealing of 2 bases ($N_1N_2$ for a primer X and $N_3N_4$ for a primer Y) at the 3' end of each of the primers constituting a primer set to a respective noncomplementary base sequence. The presence of the false peak means that, although essentially one gene transcript should be detected by a single peak (a true peak) generated by a specific single primer set containing a sequence complementary to the gene transcript, an additional peak is also generated by another primer set that is not complementary (a false peak), resulting in a state of several peaks generated for one gene transcript. The presence of such several peaks for one gene transcript affects the detection sensitivity of an expressed gene. As a result, this complicates analytical procedures for gene expression based on the gene expression profile. Thus, a method to suppress false peaks or a method to exclude false peaks from the analysis by distinguishing them is required. The method of the present invention is to improve the detection sensitivity of an expressed gene with the suppression of the occurrence of false peaks by setting the kind of primers to be used in PCR reaction and the annealing temperature of the primers to templates to a particular range.

Method of Evaluating Genuineness of Peak

The genuineness of a peak was evaluated by comparing the base sequence of an amplified PCR product corresponding to a certain gene obtained by using primers having known sequences, with the base sequence of the gene having a known sequence registered in the existing database to determine whether or not there is a coincidence between the portions in both of the base sequences corresponding to 2 bases ($N_1N_2$ for a primer X and $N_3N_4$ for a primer Y) at the 3' end of each of the primers.

Specifically, the genuineness of a peak was evaluated according to the following procedures:

1. Using a certain primer set composed of primers X and Y having known sequences, a gene expression profile was prepared by a HiCEP method to determine the sequence of an amplified PCR product corresponding to a peak appearing in the profile.

2. A region corresponding to the base sequences of the primers X and Y used was identified from the sequence of the amplified PCR product, and only the portion of a base sequence containing the identified regions and sandwiched between these regions was selected, for which a computer-based homology search of base sequences (BLAST) was performed with respect to the existing database. The genuineness was then evaluated for three criteria (1) to (3) described below.

Incidentally, a "sense strand of a gene registered in the database" in the "base sequence of the gene registered in the database" mentioned in the description below refers to a strand having a sequence homologous to the sense strand of a fragment of a double-stranded sequence obtained in the step (h), which is to be used as a template in the PCR reaction. An "antisense strand of the gene registered in the database" refers to a strand having a sequence homologous to the antisense strand of the fragment of the double-stranded sequence obtained in the step (h), which is to be used as a template in the PCR reaction.

In addition, a "sense strand of an amplified PCR product" in the "amplified PCR product" mentioned in the description below refers to a strand having a sequence homologous to the sense strand of a fragment of a double-stranded sequence obtained in the step (h), which is to be used as a template in the PCR reaction, and an "antisense strand of the amplified PCR product" refers to a strand having a sequence homologous to the antisense strand of the fragment of the double-stranded sequence obtained in the step (h), which is to be used as a template in the PCR reaction.

(1) The base sequences of the sense strand and the antisense strand of the amplified PCR product identified by the homologous search (however, except for the portion corresponding to each primer) each agree 100% with the base sequences of the sense strand and the anti-sense strand of a certain gene (all or a portion of) registered in the database.

(2) In the sense strand of the amplified PCR product, the recognition sequence of a restriction enzyme X is present in the proximity of the 5'-end side of the region having the agreement obtained in (1), and in the antisense strand of the amplified PCR product, the recognition sequence of a restriction enzyme Y is present in the proximity of the 5'-end side of the region having the agreement obtained in (1).

(3) The sequence of 2 bases (corresponding to the base sequence of $N_1N_2$ of the primer X) at the 3'-end side immediately adjacent to the recognition sequence of the restriction enzyme X in the sense strand of the amplified PCR product evaluated in (2) agrees with the sequence of 2 bases (corresponding to the base sequence of $N_1N_2$ of the primer X) at the 3'-end side immediately adjacent to the recognition sequence of the restriction enzyme X in the sense strand of the gene registered in the database, and the sequence of 2 bases (corresponding to the base sequence of $N_3N_4$ of the primer Y) at the 3'-end side immediately adjacent to the recognition sequence of the restriction enzyme Y in the antisense strand of the amplified PCR product evaluated in (2) agrees with the sequence of 2 bases (corresponding to the base sequence of $N_3N_4$ of the primer Y) at the 3'-end side immediately adjacent to the recognition sequence of the restriction enzyme Y in the antisense strand of the gene registered in the database.

3. If an amplified PCR product constituting a certain peak satisfied all of the above-mentioned three conditions, the peak was judged to be a true peak, as obtained based on the correct annealing of primers.

On the other hand, there is a peak composed of a PCR product that satisfies the above conditions (1) and (2) but not the condition (3). If an amplification reaction proceeds based on correct annealing, an "amplified PCR product" and a "gene registered in the database" should have identical sequences in the portion corresponding to the sequence of 2 bases ($N_1N_2$ for the primer X and $N_3N_4$ for the primer Y) at the 3'-end side of each of primers. On the other hand, if an amplification reaction proceeds based on misannealing, a final "amplified PCR product" and a "gene registered in the database" are to have different sequences in the portion corresponding to the sequence of 2 bases at the 3'-end side of each of primers, because the amplification reaction further proceeds in subsequent cycles thereof using the primer that has caused misannealing as a template. Therefore, an "amplified PCR product" having a different sequence in the portion corresponding to the sequence of 2 bases at the 3'-end side of each primer from that of a "gene registered in the database" (i.e., a PCR product that does not satisfy the condition (3)) was concluded to be a PCR product obtained from the misannealing of primers, and thus a peak constituting such a PCR product was judged to be a false peak.

Example 1

For mouse embryonic fibroblasts (MEF), a gene expression profile was prepared by the following procedures:

(a) Synthesis of a Single-stranded cDNA Bearing a Tag Substance

Total RNA was extracted from 107 embryonic fibroblasts (MEF) prepared from the C3H line mouse using RNAeasy MiniKit (Qiagen) and poly(A) RNA was further extracted therefrom using Micro Fast Track Kit (Invitrogen). An oligo dT primer modified at the 5' end with biotin as a tag substance (a custom oligonucleotide synthesized by Invitrogen) was used together with the extracted poly(A) RNA as a template to synthesize a single-stranded cDNA bearing biotin at the 5' end relative to the single-stranded cDNA by using SuperScript First-Strand System (Invitrogen).

(b) Synthesis of a Double-stranded cDNA

DNA polymerase 1, Second-strand buffer and *E. coli* DNA ligase (all available from Invitrogen) were used together with the single-stranded cDNA as a template synthesized in the step (a) to synthesize a double-stranded cDNA bearing biotin at the 3'-end side relative to the double-stranded cDNA according to a method of double-stranded cDNA synthesis recommended by Invitrogen.

(c) Cleavage by a Restriction Enzyme X

The double-stranded cDNA obtained in the step (b) was cleaved with MspI as a first restriction enzyme X (TaKaRa) at 37° C. for 4 hours.

(d) Recovery of a Fragment Bearing the Tag Substance

A fragment bearing biotin was recovered from the double stranded cDNA fragments obtained in the step (c) using magnetic beads on which streptavidin as a substance having a high affinity for biotin was immobilized (DYNAL) according to the conditions recommended by DYNAL.

(e) Ligation of an Adaptor X

To the cleavage site of the double-stranded cDNA fragment recovered in the step (d) by the restriction enzyme MspI, the MspI adaptor as an adaptor X containing a sequence complementary to the sequence of the cleavage site (a custom oligo synthesis by Invitrogen):

(Base Sequence of the MspI Adaptor)
5'-AACACGAATGGCTACATGACACTCGGTT-3' (at the sense strand side of the double-stranded cDNA) (SEQ ID No.: 1);
5'-CGAACCGAGTGTCATGTAGCCATTCGTGTT-3' (at the antisense strand side of the double-stranded cDNA) (SEQ ID NO.: 2), was ligated at 16° C. over 16 hours or more using T4 DNA Ligase (NEB (New England Biolabs)) to obtain a fragment ligated with the MspI adaptor at the 5'-end side relative to the double-stranded cDNA.

(f) Cleavage by a Second Restriction Enzyme Y

The fragment of the double-stranded cDNA recovered in the step (e) was cleaved with MseI as a second restriction enzyme Y (NEB) at 37° C. for 4 hours.

(g) Recovery of a Fragment Containing the Cleavage Site by the Second Restriction Enzyme Y The fragment bearing biotin was removed from the double stranded cDNA fragments obtained in the step (f) using magnetic beads on which streptavidin was immobilized (DYNAL) according to the method recommended by DYNAL, and the fragment containing the cleavage site by the second restriction enzyme Y was recovered. The obtained double-stranded cDNA fragment contained the MspI adaptor at the 5' end and the cleavage site by the restriction enzyme MspI at the 3' end.

(h) Ligation of an Adaptor Y

To the cleavage site of the double-stranded cDNA fragment recovered in the step (g) by the restriction enzyme MseI, the MseI adaptor as an adaptor Y containing a sequence complementary to the sequence of the cleavage site (Custom Oligo Synthesis by Invitrogen):

(Base Sequence of the MseI Adaptor)
5'-AGTCACGAGTATCATACTGCGGGCGTCC-3' (at the antisense strand side of the double-stranded cDNA) (SEQ ID No.: 3);
5'-TAGGACGCCCGCAGTATGATACTCGTGACT-3' (at the sense strand side of the double-stranded cDNA) (SEQ ID NO.: 4), was ligated at 25° C. for 16 hours or more using T4 DNA Ligase (NEB) to obtain a fragment ligated with the MseI adaptor at the 3'-end side relative to the double-stranded cDNA. Excessive amount of the adaptor was removed by precipitation using ethanol.

(i) PCR Reaction Using Primers X and Y (1) Synthesis of Primers X and Y

As a primer X, 16 different MspI primers each composed of 20 bases:

(Base Sequence of the MseI Primer)
5'-ACATGACACTCGGTTCGGN$_1$N$_2$-3'

(wherein N$_1$N$_2$ is CC, CT, CG, CA, TC, TT, TA, TG, AC, AA, AG, AT, GT, GC, GA, or GG) (SEQ ID NO.: 5)

were synthesized depending on the kinds of N$_1$N$_2$ by the custom oligo synthesis (invitrogen).

As a primer Y, 16 different MseI primers each composed of 20 bases:

(Base Sequence of the MseI Primer)
5'-ATACTGCGGGCGTCCTAAN$_3$N$_4$-3'

(wherein N$_3$N$_4$ is CC, CT, CG, CA, TC, TT, TA, TG, AC, AA, AG, AT, GT, GC, GA, or GG) (SEQ ID NO.: 6)

were synthesized depending on the kinds of N$_3$N$_4$ according to the same method as the MspI primer.

Moreover, the MspI primers were labeled with the fluorescent labeling substances named FAM, NED, or HEX by the custom oligo synthesis (Invitrogen).

The resulting MseI primers (16 different types) and MspI primers (16 different types) were combined to construct a total of 256 (16×16) different pairs of primers (primer sets).

The Tm values of the primers constituting the 256 (16×16; MseI primers (16 different types) and MspI primers (16 different types)) different primer sets in total were different depending on each sequence of 2 bases (N$_1$N$_2$ for the primer X and N$_3$N$_4$ for the primer Y) at the 3'-end side. However the values were in the range of 60° C. to 64° C. according to the above-described calculation formula (1). Consequently, the TmMax value was set at 64° C.

(2) PCR Reaction

The obtained 256 different primer sets were used to carry out a PCR reaction with the fragment of the double-stranded sequence obtained in the step (h) as a template and TITANIUM Taq DNA Polymerase (Clontech) under the conditions described below. An optimum temperature of the polymerase used is in the range of 72° C. to 74° C. The annealing temperature was 70° C. (TmMAX+6° C.).

The PCR conditions:
At 95° C. for 1 min;
(at 98° C. for 20 sec, at 70° C. for 30 sec and at 72° C. for 1 min)×28 times; and
at 60° C. for 30 sec.

(j) Preparation of a Gene Expression Profile

PCR products obtained in the step (h) were subjected to electrophoresis using PRISM 3100 Capillary Electrophoresis Device (Applied Biosystems) according to the protocol recommended by POP4 to detect the migration distance and peaks. Based on the results of the electrophoresis, software GeneScan™ (Applied Biosystems, Japan) was used to prepare a gene expression profile showing the migration distance indicative of the molecular weight on the horizontal axis and the expression level indicative of the fluorescent intensity on the vertical axis.

Figure 2:
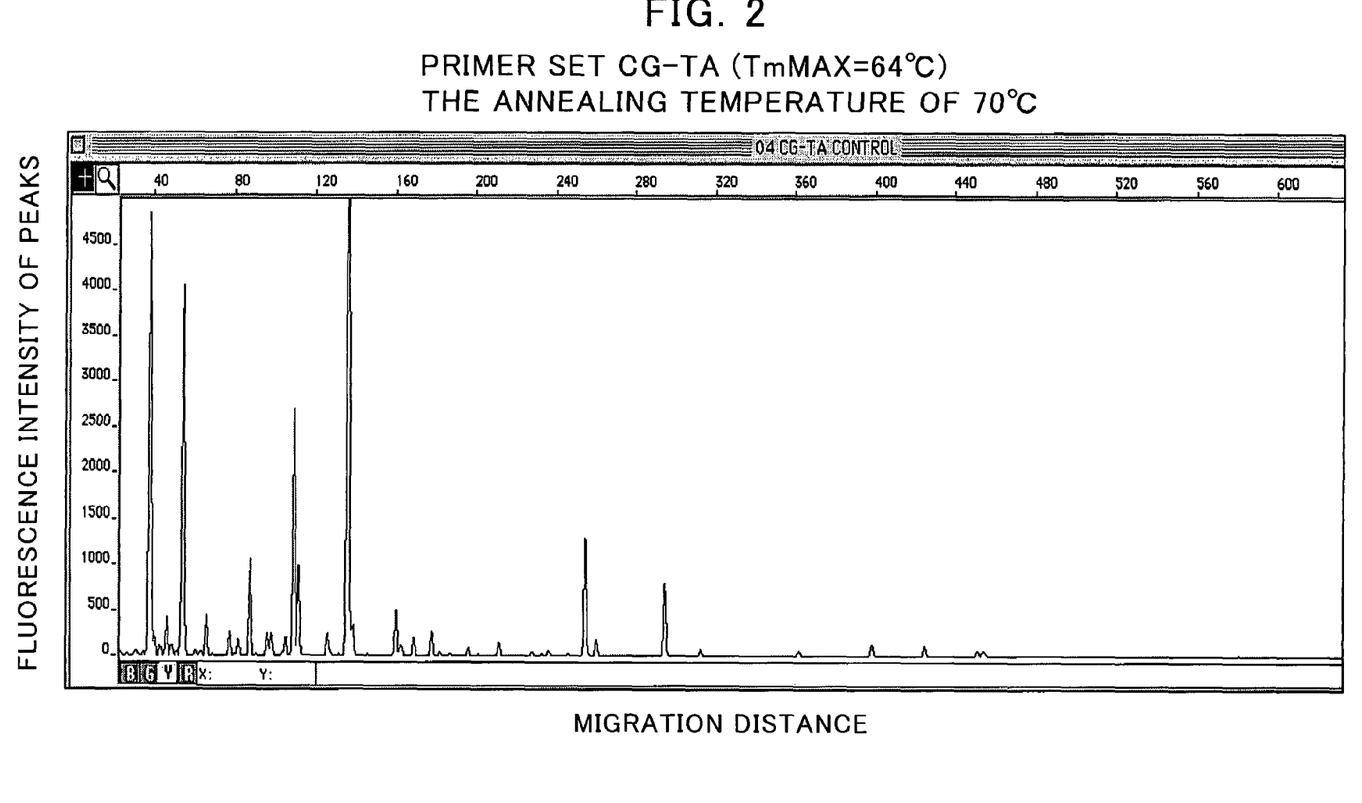
FIG. 2 is a diagram showing a gene expression profile prepared according to the present invention.

FIG. 2 shows a gene expression profile obtained by using a primer set composed of the following MspI primer (primer X) and MseI primer (primer Y):

```
(MspI primer)
5'-ACATGACACTCGGTTCGGCG-3';   (SEQ ID NO.: 7)

(MseI primer)
5'-ATACTGCGGGCGTCCTAATA-3'.   (SE1 ID NO.: 8)
```

In FIG. 2, the vertical axis represents the fluorescent intensity of a peak indicating an amplified PCR product and correlates with the final quantity of the amplified PCR product. The horizontal axis represents the migration distance of the amplified PCR product and correlates with the number of nucleotide residues constituting the amplified PCR product (corresponding to a gene) of each peak. That is, the magnitude of a peak appearing in the profile shows the quantity of an amplified PCR product corresponding to the peak, i.e., the expression level of a gene corresponding to the amplified PCR product. Therefore, by observing changes in the magnitude of a particular peak, the frequency of the expression of the corresponding gene can be analyzed.

Example 2

A primer set composed of primers X and Y shown below was used to prepare a gene expression profile for the mouse embryonic fibroblast (MEF) according to the steps similar to those in Example 1 except that the temperature for annealing the primers to templates was changed to 70° C.-76° C. (in 1° C. increments).

```
MspI primer as the primer X (20 bases):
5'-ACATGACACTCGGTTCGGTA-3';   (SEQ ID NO.: 9)

MseI primer as the primer Y (20 bases):
5'-ATACTGCGGGCGTCCTAACC-3'.   (SEQ ID NO.: 10)
```

Because the Tm of the MspI primer was 60° C. and the Tm of the MseI primer was 64° C. according to the above-described calculation formula (1), the primer TmMAX was set to 64° C. Thus, the annealing temperature of 70° C. to 76° C. used in Example 2 corresponded to TmMAX+6° C. to TmMAX+12° C. of the primer.

Comparative Example 1

The same primers used in Example 2 were used to prepare a gene expression profile for the mouse embryonic fibroblast (MEF) according to the steps similar to those in Example 2 except that the annealing temperature for the primers to templates was changed to the range of 67° C. (TmMAX+3° C.) to 69° C. (Tm MAX+5° C.) (in 1° C. increments).

Test Example 1

Figure 3:
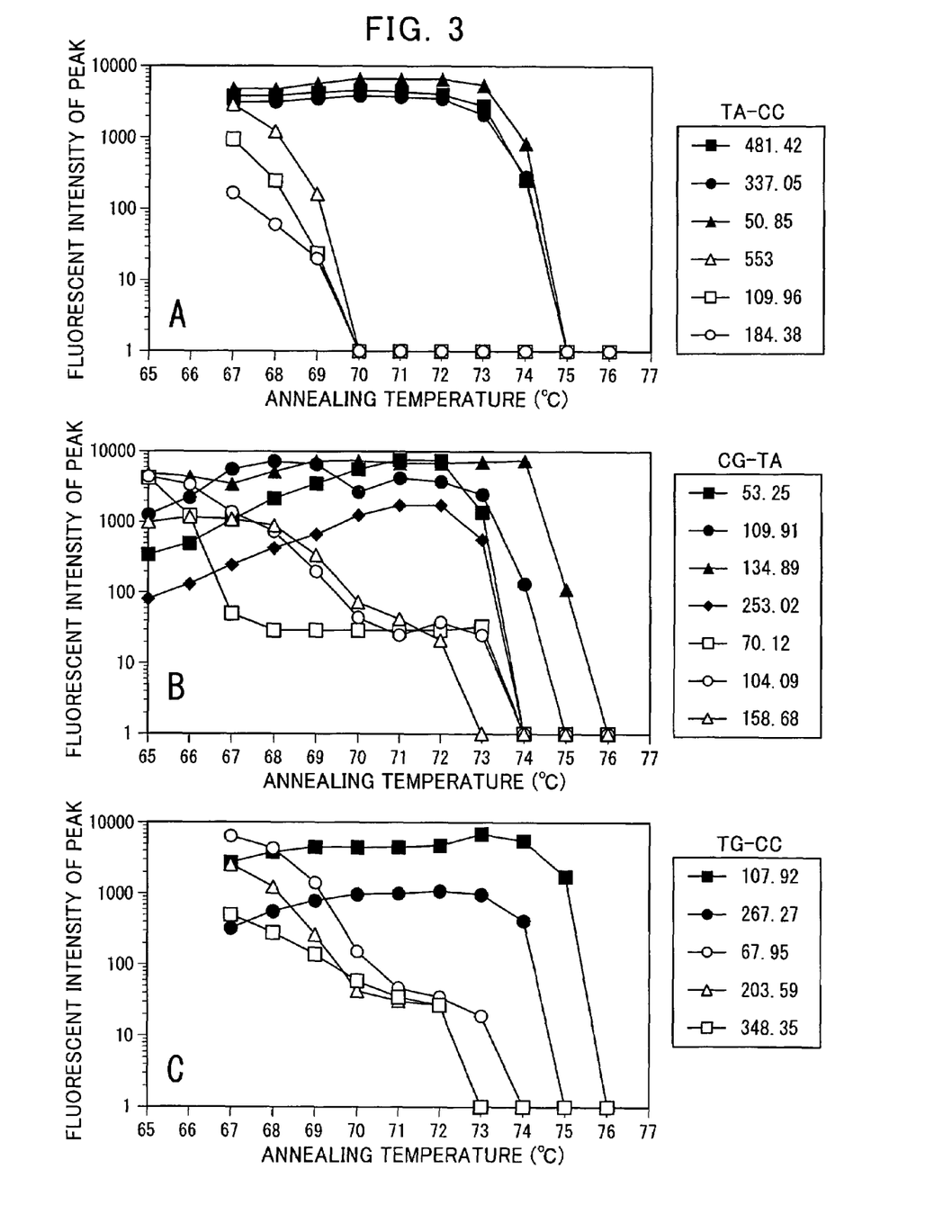
FIG. 3 is a graph showing the relationship between the annealing temperature and the fluorescent intensity of peaks.

Regarding six peaks randomly extracted from the gene expression profiles obtained in Example 2 and Comparative Example 1 (however, each of the peaks corresponds to the expression of the identical gene in Example 2 and Comparative Example 1), the relationship between the annealing temperature and the fluorescent intensity of the peak is illustrated (FIG. 3A). In the figure, the horizontal axis represents the annealing temperature and the vertical axis represents the fluorescent intensity of the peak of the amplified PCR product (corresponding to the quantity of the amplified PCR product and thus to the expression level of the gene).

The six peaks were roughly classified into 2 groups Group 1 and Group 2: in Group 1, peaks maintained high fluorescent intensity (high detection sensitivity) even at annealing temperatures of 70° C. or more (the legends in the figure: ■, ●, and ▲, where the numbers next to the legends show the degree of migration of an amplified PCR product corresponding to each peak (the value obtained from calibration by a size-standard marker subjected to electrophoresis simultaneously with the amplified PCR product sample, that is, the value approximately equivalent to the length of a gene fragment corresponding to the amplified PCR product)); in Group 2, the fluorescent intensity of peaks decreased below a detection limit (the value of fluorescent intensity distinguishable from background) (i.e., the fluorescent intensity of 50 or less) at an annealing temperature of 70° C. (the legends in the figure: ◇, □, and ○).

Here, for evaluating the genuineness of each peak, the sequence of a PCR product corresponding to each peak was determined using PRISM 3100 Autosequencer. Based on the obtained base sequence, the genuineness of each peak was evaluated according to the above-described method for evaluating the genuineness of a peak. Incidentally, the existing database utilized in the evaluation was the publicly available mouse EST database (Genbank, EMBL, and DDBJ).

As a result, it was found that the peak of Group 1 is a true peak composed of the amplified PCR product that satisfies all of the conditions (1) to (3) in the above-described method for evaluating the genuineness of a peak and that the peak of Group 2 is a false peak composed of the amplified PCR product that satisfies the conditions (1) to (2) but not the condition (3).

These results indicate that, when the annealing of primers to templates in a PCR reaction is carried out at temperatures higher than TmMAX+6° C. (64° C.+6° C.=70° C.) of the primer, it is possible to decrease false peaks, and when the annealing is carried out particularly in the temperature range of TmMAX+6° C. (64° C.+6° C.=70° C.) to TmMAX+9° C. (64° C.+9° C.=73° C.), it is possible to decrease false peaks while sufficiently maintaining the detection sensitivity of true peaks, resulting in further improvement in the detection sensitivity of the HiCEP method.

Example 3

A primer set composed of primers X and Y shown below was used to prepare a gene expression profile for the mouse embryonic fibroblast (MEF) according to the steps similar to those in Example 1 except that the annealing temperature for the primers to templates was changed to 70° C.-76° C. (in 1° C. increments).

```
MspI primer as the X primer (20 bases):
5'-ACATGACACTCGGTTCGGCG-3';    (SEQ ID NO.: 11)

MseI primer as the primer Y (20 bases):
5'-ATACTGCGGGCGTCCTAATA-3'.    (SEQ ID NO.: 12)
```

Because Tm of the MspI primer was 64° C. and the Tm of the MseI primer was 60° C. according to the above-described calculation formula (1), TmMAX of the primer was set at 64° C. Thus, the annealing temperature of 70° C. to 76° C. used in Example 3 corresponded to TmMAX+6° C. to TmMAX+12° C. of the primer.

Comparative Example 2

The same primers used in Example 3 were used to prepare a gene expression profile for the mouse embryonic fibroblast (MEF) according to the steps similar to those in Example 3 except that the annealing temperature for the primers to templates was changed to the range of 65° C. (TmMAX+1° C.) to 69° C. (TmMAX+5° C.) (in 1° C. increments).

Test Example 2

Regarding seven peaks randomly extracted from the obtained gene expression profiles, the relationship between the annealing temperature and the fluorescent intensity of the peak is illustrated in the same manner as FIG. 3A (FIG. 3B).

The seven peaks were roughly classified into 2 groups of Group 1 and Group 2: in Group 1, peaks maintained high fluorescent intensity (high detection sensitivity) even at annealing temperatures of 70° C. or more (the legends in the figure: ■, ●, ▲, and ◆); and in Group 2, the fluorescent intensity of peaks decreased below a detection limit (the fluorescent intensity of 50 or less ) at an annealing temperature of 70° C. (the legends in the figure. □, ○, and △).

The genuineness of each peak was evaluated in the manner similar to Test Example 1. As a result, it was found that the peak of Group 1 is a true peak composed of the amplified PCR product that satisfied all of the conditions (1) to (3) in the above-described method for evaluating the genuineness of a peak and that the peak of Group 2 is a false peak composed of the amplified PCR product that satisfied the conditions (1) to (2) but not the condition (3).

These results indicate that, when the annealing of primers to templates in a PCR reaction is carried out at temperatures higher than TmMAX+6° C. (64° C.+6° C.=70° C.) of the primer, it is possible to decrease false peaks, and when the annealing is carried out particularly in the temperature range of TmMAX+6° C. (64° C.+6° C.=70° C.) to TmMAX+9° C. (64° C.+9° C.=73° C.), it is possible to decrease false peaks while sufficiently maintaining the detection sensitivity of true peaks, resulting in further improvement in the detection sensitivity of the HiCEP method.

Example 4

A primer set composed of primers X and Y shown below was used to prepare a gene expression profile for the mouse embryonic fibroblast (MEF) according to the steps similar to those in Example 1 except that the annealing temperature for the primers to templates was changed to 70° C.-76° C. (in 1° C. increments).

```
MspI primer as the primer X (20 bases):
5'-ACATGACACTCGGTTCGGTG-3';    (SEQ ID NO.: 13)

MseI primer as the primer Y (20 bases):
5'-ATACTGCGGGCGTCCTAACC-3'.    (SEQ ID NO.: 14)
```

Because Tm of the MspI primer was 62° C. and Tm of the MseI primer was 64° C. according to the above-described calculation formula (1), primer TmMAX was set at 64° C. Thus, the annealing temperature of 70° C. to 76° C. used in Example 4 corresponded to TmMAX+6° C. to TmMAX+12° C. of the primer.

Comparative Example 3

The same primers used in Example 4 were used to prepare a gene expression profile for the mouse embryonic fibroblast (MEF) according to the steps similar to those in Example 4 except that the annealing temperature for the primers to templates was changed to the range of 67° C. (TmMAX+3° C.) to 69° C. (TmMAX+5° C.) (in 1° C. increments).

Test Example 3

Regarding five peaks randomly extracted from the obtained gene expression profiles, the relationship between the annealing temperature and the fluorescent intensity of the peak is illustrated in the same manner as FIG. 3A (FIG. 3C).

The five peaks were roughly classified into 2 groups, Group 1 and Group 2: in Group 1, peaks maintained high fluorescent intensity (high detection sensitivity) even at annealing temperatures of 70° C. or more (the legends in the figure: ■ and ●); and in Group 2, the fluorescent intensity of peaks decreased below a detection limit (the fluorescent intensity of 50 or less) at an annealing temperature of 70° C. (the legends in the figure: ○, Δ, and □).

The genuineness of each peak was evaluated in the manner similar to Test Example 1. As a result, it was found that the peak of Group I is a true peak composed of the amplified PCR product that satisfied all of the conditions (1) to (3) in the above-described method for evaluating the genuineness of a peak and that the peak of Group 2 is a false peak composed of the amplified PCR product that satisfied the conditions (1) to (2) but not the condition (3).

These results indicate that, when the annealing of primers to templates in a PCR reaction is carried out at temperatures higher than TmMAX+6° C. (64° C.+6° C.=70° C.) of the primer, it is possible to decrease false peaks, and when the annealing is carried out particularly in the temperature range of TmMAX+6° C. (64° C.+6° C.=70° C.) to TmMAX+9° C. (64° C.+9° C.=73° C.), it is possible to decrease false peaks while sufficiently maintaining the detection sensitivity of true peaks, resulting in further improvement in the detection sensitivity of the HiCEP method.

INDUSTRIAL APPLICABILITY

According to the present invention, the occurrence of false peaks resulting from the misannealing of primers in the process for preparing a gene expression profile can be decreased. Thus, the detection sensitivity of expressed genes is improved, enabling preparation of a gene expression profile with high precision.

The magnitude of a peak appearing on a gene expression profile prepared according to the present invention reflects the expression level of an expressed gene in a subject cell. Consequently, by observing changes in the magnitude of the peak, the frequency of gene expression can be analyzed. It is possible to carry out, for example, comparison between a normal cell and an abnormal cell, comparison between a normal cell and a canceer cell, comparison between different cells, and comparison between cells treated under different conditions.

---

The invention claimed is:

1. A method for preparing a gene expression profile, which comprises:

(a) synthesizing a single-stranded cDNA by using a poly (A) RNA as a template, wherein a single-stranded cDNA bearing a tag substance at the 5'-end side relative to the single-stranded cDNA is synthesized;

(b) synthesizing a double-stranded cDNA by using the single-stranded cDNA synthesized in the step (a) as a template, wherein a double-stranded cDNA bearing a tag substance at the 3'-end side relative to the double-stranded cDNA is obtained;

(c) cleaving the double-stranded cDNA obtained in the step (b) with a first restriction enzyme X;

(d) recovering a fragment bearing the tag substance from fragments obtained in the step (c) by using a substance having a high affinity for the tag substance;

(e) ligating an adaptor X containing a sequence complementary to the sequence of the cleavage site and a sequence complementary to the sequence of a primer X to the cleavage site of the fragment generated by the first restriction enzyme X as recovered in the step (d), to obtain a fragment ligated with the adaptor X at the 5'-end side relative to the double-stranded cDNA;

(f) cleaving the fragment recovered in the step (e) with a second restriction enzyme Y that does not cleave the adaptor X;

(g) removing a fragment bearing the tag substance from the fragments obtained in the step (f) by using a substance having a high affinity for the tag substance, to recover a fragment containing the cleavage site generated by the second restriction enzyme Y at the 3'-end side relative to the double-stranded cDNA;

(h) ligating an adaptor Y containing a sequence complementary to the sequence of the cleavage site and a sequence complementary to the sequence of a primer Y to the cleavage site of the fragment generated by the second restriction enzyme Y as recovered in the step (g), to obtain a fragment of a double-stranded sequence ligated with the adaptor Y at the 3'-end side relative to the double-stranded cDNA;

(i) performing a PCR reaction with the fragment of the double-stranded sequence obtained in the step (h) as a template by using a primer set composed of a primer X containing a sequence complementary to the sequence of the adaptor X, which has the sequence of 2 bases $N_1N_2$ at the 3'-end side relative to the primer X, wherein $N_1$ and $N_2$ may be identical or different bases that are selected from the group consisting of adenine, thymine, guanine and cytosine, and a primer Y containing a sequence complementary to the sequence of the adaptor Y, which has the sequence of 2 bases $N_3N_4$ at the 3'-end side relative to the primer Y, wherein $N_3$ and $N_4$ may be identical or different bases that are selected from the group consisting of adenine, thymine, guanine and cytosine; and (j) subjecting the obtained PCR product to electrophoresis and detecting the migration distance and peaks to prepare a gene expression profile, wherein, in the step (i), the annealing of the primer X and the primer Y to the adaptor X and the adaptor Y respectively is carried out in the temperature range of TmMAX+6° C. to TmMAX+14° C. of the primer, wherein Tm is calculated by the formula: Tm(° C.)=2×(A+T)+4×(G+C) wherein (A+T) is the sum of the numbers of adenine (A) and thymine (T) residues comprising a primer and (G+C) is the sum of the numbers of cytosine (C) and guanine (G) residues comprising a primer;

wherein, in the step (i), 256 different primer sets composed of 16 different primers X and 16 different primers Y in combination are used as primer set; and wherein, in the step (i), the primer X is 5'-ACATGACACTCGGTTCGG$N_1N_2$-3', wherein $N_1N_2$ is CC, CT, CG, CA, TC, TT, TA, TG, AC, AA, AG, AT, GT, GC, GA, or GG; and the primer Y is 5'-ATACTGCGGGCGTCCTAA$N_3N_4$-3', wherein $N_3N_4$ is CC, CT, CG, CA, TC, TT, TA, TG, AC, AA, AG, AT, GT, GC, GA, or GG.

2. The method for preparing the gene expression profile according to claim 1, wherein, in the step (i), the annealing of the primer X and the primer Y to the adaptor X and the adaptor Y respectively is carried out in the temperature range of TmMAX+6° C. to TmMAX+9° C.

3. A method for analyzing the frequency of a gene expression, which comprises:

(a) synthesizing a single-stranded cDNA by using a poly (A) RNA as a template, wherein a single-stranded cDNA bearing a tag substance at the 5'-end side relative to the single-stranded cDNA is synthesized;

(b) synthesizing a double-stranded cDNA by using the single-stranded cDNA synthesized in the step (a) as a template, wherein a double-stranded cDNA bearing a tag substance at the 3'-end side relative to the double-stranded cDNA is obtained;

(c) cleaving the double-stranded cDNA obtained in the step (b) with a first restriction enzyme X;

(d) recovering a fragment bearing the tag substance from the fragments obtained in the step (c) by using a substance having a high affinity for the tag substance;

(e) ligating an adaptor X containing a sequence complementary to the sequence of the cleavage site and a sequence complementary to the sequence of a primer X to the cleavage site of the fragment generated by the first restriction enzyme X and recovered in the step (d), to obtain a fragment ligated with the adaptor X at the 5'-end side relative to the double-stranded cDNA;

(f) cleaving the fragment recovered in the step (e) with a second restriction enzyme Y that does not cleave the adaptor X;

(g) removing a fragment bearing the tag substance from the fragments obtained in the step (f) by using a substance having a high affinity for the tag substance to recover a fragment containing the cleavage site generated by the second restriction enzyme Y at the 3'-end side relative to the double-stranded cDNA;

(h) ligating an adaptor Y containing a sequence complementary to the sequence of the cleavage site and a sequence complementary to the sequence of a primer Y to the cleavage site of the fragment generated by the second restriction enzyme Y as recovered in the step (g), to obtain a fragment of a double-stranded sequence ligated with the adaptor Y at the 3'-end side relative to the double-stranded cDNA;

(i) performing a PCR reaction with the fragment of the double-stranded sequence obtained in the step (h) as a template by using a primer set composed of a primer X containing a sequence complementary to the sequence of the adaptor X, which has the sequence of 2 bases $N_1N_2$ at the 3'-end side relative to the primer X, wherein $N_1$ and $N_2$ may be identical or different bases that are selected from the group consisting of adenine, thymine, guanine and cytosine, and a primer Y containing a sequence complementary to the sequence of the adaptor Y, which has the sequence of 2 bases $N_3N_4$ at the 3'-end side relative to the primer Y, wherein $N_3$ and $N_4$ may be identical or different bases that are selected from the group consisting of adenine, thymine, guanine and cytosine;

(j) subjecting the obtained PCR product to electrophoresis and detecting the migration distance and peaks to prepare a gene expression profile, and (k) analyzing changes of the frequency of the gene expression of a subject cell by comparing two gene expression profiles obtained in the steps (a) to (i), wherein, in the step (i), the annealing of the primer X and the primer Y to the adaptor X and the adaptor Y respectively is carried out in the temperature range of TmMAX+6° C. to TmMAX+14° C. of the primer, wherein Tm is calculated by the formula: Tm(° C.)=2×(A+T)+4×(G+C) wherein (A+T) is the sum of the numbers of adenine (A) and thymine (T) residues comprising a primer and (G+C) is the sum of the numbers of cytosine (C) and guanine (G) residues comprising a primer;

wherein in the step (i), 256 different primer sets composed of 16 different primers X and 16 different primers Y in combination are used as primer set; and wherein, in the step (i), the primer X is 5'-ACATGACACTCGGTTCGGN$_1$N$_2$-3', wherein N$_1$N$_2$ is CC, CT, CG, CA, TC, TT, TA, TG, AC, AA, AG, AT, GT, GC, GA, or GG; and the primer Y is 5'-ATACTGCGGGCGTCCTAAN$_3$N$_4$-3', wherein N$_3$N$_4$ is CC, CT, CG, CA, TC, TT, TA, TG, AC, AA, AG, AT, GT, GC, GA, or GG.

* * * * *

SEQUENCE LISTING

```
<160> NUMBER OF SEQ ID NOS: 14

<210> SEQ ID NO 1
<211> LENGTH: 28
<212> TYPE: DNA
<213> ORGANISM: Artificial
<220> FEATURE:
<223> OTHER INFORMATION: PCR adapter

<400> SEQUENCE: 1
aacacgaatg gctacatgac actcggtt                                        28

<210> SEQ ID NO 2
<211> LENGTH: 30
<212> TYPE: DNA
<213> ORGANISM: Artificial
<220> FEATURE:
<223> OTHER INFORMATION: PCR adapter

<400> SEQUENCE: 2
cgaaccgagt gtcatgtagc cattcgtgtt                                      30

<210> SEQ ID NO 3
<211> LENGTH: 28
<212> TYPE: DNA
<213> ORGANISM: Artificial
<220> FEATURE:
<223> OTHER INFORMATION: PCR adapter

<400> SEQUENCE: 3
agtcacgagt atcatactgc gggcgtcc                                        28
```

```
<210> SEQ ID NO 4
<211> LENGTH: 30
<212> TYPE: DNA
<213> ORGANISM: Artificial
<220> FEATURE:
<223> OTHER INFORMATION: PCR adapter

<400> SEQUENCE: 4
taggacgccc gcagtatgat actcgtgact                                              30

<210> SEQ ID NO 5
<211> LENGTH: 20
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (19)..(20)
<223> OTHER INFORMATION: n is a, t, g or c

<400> SEQUENCE: 5
acatgacact cggttcggnn                                                         20

<210> SEQ ID NO 6
<211> LENGTH: 20
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (19)..(20)
<223> OTHER INFORMATION: n is a, t, g or c

<400> SEQUENCE: 6
atactgcggg cgtcctaann                                                         20

<210> SEQ ID NO 7
<211> LENGTH: 20
<212> TYPE: DNA
<213> ORGANISM: Artificial
<220> FEATURE:
<223> OTHER INFORMATION: PCR primer

<400> SEQUENCE: 7
acatgacact cggttcggcg                                                         20

<210> SEQ ID NO 8
<211> LENGTH: 20
<212> TYPE: DNA
<213> ORGANISM: Artificial
<220> FEATURE:
<223> OTHER INFORMATION: PCR primer

<400> SEQUENCE: 8
atactgcggg cgtcctaata                                                         20

<210> SEQ ID NO 9
<211> LENGTH: 20
<212> TYPE: DNA
<213> ORGANISM: Artificial
<220> FEATURE:
<223> OTHER INFORMATION: PCR primer

<400> SEQUENCE: 9
acatgacact cggttcggta                                                         20
```

```
<210> SEQ ID NO 10
<211> LENGTH: 20
<212> TYPE: DNA
<213> ORGANISM: Artificial
<220> FEATURE:
<223> OTHER INFORMATION: PCR primer

<400> SEQUENCE: 10
atactgcggg cgtcctaacc                                               20

<210> SEQ ID NO 11
<211> LENGTH: 20
<212> TYPE: DNA
<213> ORGANISM: Artificial
<220> FEATURE:
<223> OTHER INFORMATION: PCR primer

<400> SEQUENCE: 11
acatgacact cggttcggcg                                               20

<210> SEQ ID NO 12
<211> LENGTH: 20
<212> TYPE: DNA
<213> ORGANISM: Artificial
<220> FEATURE:
<223> OTHER INFORMATION: PCR primer

<400> SEQUENCE: 12
atactgcggg cgtcctaata                                               20

<210> SEQ ID NO 13
<211> LENGTH: 20
<212> TYPE: DNA
<213> ORGANISM: Artificial
<220> FEATURE:
<223> OTHER INFORMATION: PCR primer

<400> SEQUENCE: 13
acatgacact cggttcggtg                                               20

<210> SEQ ID NO 14
<211> LENGTH: 20
<212> TYPE: DNA
<213> ORGANISM: Artificial
<220> FEATURE:
<223> OTHER INFORMATION: PCR primer

<400> SEQUENCE: 14
atactgcggg cgtcctaacc                                               20
```